United States Patent [19]

Nakamura-Craig et al.

[11] Patent Number: 5,712,277
[45] Date of Patent: Jan. 27, 1998

[54] USE OF 3,5-DIAMINO-6-(2,3-DICHLOROROPHENYL) -1,2,4-TRIAZINE FOR THE TREATMENT OF PAIN AND OEDEMA

[75] Inventors: Meire Nakamura-Craig; Michael John Leach, both of Beckenham, Great Britain

[73] Assignee: Glaxo Wellcome Inc., Research Triangle Park, N.C.

[21] Appl. No.: 680,111

[22] Filed: Jul. 15, 1996

Related U.S. Application Data

[63] Continuation of Ser. No. 284,497, filed as PCT/GB93/00341 Feb. 2, 1993.

[30] Foreign Application Priority Data

Feb. 19, 1992 [GB] United Kingdom ................ 9203483

[51] Int. Cl.$^6$ .................................................. A01N 43/64
[52] U.S. Cl. ............................................................ 514/242
[58] Field of Search ............................................... 514/242

[56] References Cited

U.S. PATENT DOCUMENTS

| | | | |
|---|---|---|---|
| 3,637,688 | 1/1972 | Rees et al. | 260/249.9 |
| 4,310,551 | 1/1982 | Gullo et al. | 424/249 |
| 4,847,249 | 7/1989 | Sawyer et al. | 514/242 |

FOREIGN PATENT DOCUMENTS

| | | |
|---|---|---|
| 0 021 121 A1 | 1/1981 | European Pat. Off. . |
| 0 247 892 A1 | 12/1987 | European Pat. Off. . |
| 0 459 829 A1 | 12/1991 | European Pat. Off. . |

OTHER PUBLICATIONS

Pain 23, (1985) 73–82 Posner et al. "Effects of an Opiate on Cold–induced Pain and the CNS in Healthy Volunteers".
Epilepsia: vol. 27, no. 5, 1986 pp. 490–497; M.J. Leach et al.; "Pharmacological Studies On Lamotrigine, A Novel Potential Antiepileptic Drug: ii. Neurochemical Studies on The Mechanism Of Action".
Neuroscience Letters; vol. 112, No. 2,3 1990; pp. 348–351; E.G. McGeer et al.; "Lamotrigine Protects Against Kainate But Not Ibotenate Lesions In Rat Striatum".
Trends In Pharmcological Sciences; vol. 11; 1990, pp. 307–309; A.H. Dickenson; "A Cure For Wind Up: NMDA Receptor Antagonists As Potential Analgesics".
European Journal of Pharmacology; vol. 187; No. 3, 1990, pp. 513–518; P. Klepstad et al. "Evidence Of A Role For NMDA Receptors In Pain Perception".
Annals of N.York Acad. Of Scien; vol. 648; 1992, pp. 368–370; G.D. Zeevalk et al.; "NMDA Receptors Cellular Edema, And Metabolic Stress And Conference On Neurotoxins And Their Potential Roles In Neurodegeneration" May 8, 1991. N. York.
Advances in Neurology; vol. 52; 1990; pates 219–222; O. Kempski et al. "Intravenous Glutamate Enhances Edema Formation After A Freezing Lesion".
British Journal of Pharmacology; vol. 106, 1992; p. 50P. N. Nakamura–Craig et al.; "Analegesic Effects Of The Glutamate Release Inhibitor, Lamotrigine In The Rat".
British Journ. of Pharmacology; vol. 107, no. supl. 1992; p. 337P; M. Nakamura–Craig et al.; "Analgesic Effects Of Lamotrigine In An Experimental Model Of Neuropathic Pin In Rats".
Advances in Pain Research and Therapy; vol. 7, 1984 pp. 147–151; L.M. Halpern: "Drugs In The Management Of Pain: Pharmacology And Appropriate Strategies Of Clinical Utilization".
Abstract Of The 14Th Annual Meeting Of The European Neuroscience Associate; Cambridge 8–12; Sept. 1991; two pages.
Br. Anaesth; 1989; vol. 63; pp. 139–146; c.J. Woolf: "Recent Advances In The Pathophysiology Of Acute Pain".
Pain; vol. 38; 1989; pp. 91–98; M. Nakamura–Craig et al.; "Substance P and Peripheral Inflammatory Hyperalgesia".
Pain; vol. 42; 1990; pp. 365–371; S.H. Ferreira; "Induction, Blockade And Restoration Of A Persistent Hypersensitive State".
Neuroscience Letters; vol. 124; 1991; pp. 49–51; M. Nakamura–Craig et al.; "Effect Of Neurokinin A, Substance P And Calcitonin Gene Related Peptide In Peripheral Hyperalgesia In The Rat Paw".
European Search Report.

*Primary Examiner*—Paul J. Killos
*Attorney, Agent, or Firm*—Nixon & Vanderhye

[57] ABSTRACT

The present invention relates to the use of 3,5-diamino-6-(2,3-dichlorophenyl)-1,2,4-triazine and its pharmaceutically and veterinarily acceptable acid addition salts in therapy.

8 Claims, 10 Drawing Sheets

USE OF 3,5-DIAMINO-6-(2,3-DICHLOROROPHENYL) -1,2,4-TRIAZINE FOR THE TREATMENT OF PAIN AND OEDEMA

This application is a continuation of Ser. No. 08/284,497 filed Aug. 4, 1994, which is a 371 of PCT/GB93/00341 filed Feb. 2, 1993.

EP-A- 0021121 describes a group of triazines, including 3,5-diamino-6-(2,3-dichlorophenyl)-1,2,4-triazine, which are active in the treatment of disorders of the central nervous system, for example psychiatric and neurological disorders, and which are particularly useful as anticonvulsants, for instance in the treatment of epilepsy. These triazines are non-depressant and are therefore advantageous compared with depressant anti-epileptics such as phenobarbitone. EP-A-0247892 describes the salt of these triazines with isethionic acid, a particularly preferred salt owing to its good solubility.

One of the commonest symptoms causing a patient to consult a medical practitioner is pain. Considerable time and effort have therefore been devoted to investigating the underlying pathophysiological mechanisms of pain and researching new types of pain management. However, there is still no single form of satisfactory relief for all types of pain. There is accordingly a continuing demand for new and effective analgesics.

Relieving pain is not straightforward since the whole notion of pain embraces phenomena having different underlying causative mechanisms and different manifestations. Pain can arise in different ways, for example following certain alterations of neurological structure and function. Metabolic changes associated with diabetes or mercury poisoning, for instance, may produce a painful peripheral neuropathy. Viral damage, such as in Herpes Zoster, late poliomyelitis or Guillian-Barre's disease, may also produce painful states. Trauma to peripheral nerves can lead to neuropathic pain from neuromas, causalgia (a form of neuralgia in which there is a sensation of localised burning pain) or phantom pain.

Current pain management includes treatment with carbamazepine, and with opioid analgesics such as morphine and morphine-like drugs, these are typically used to treat moderate to sever pain. However, one major problem associated with their use is that tolerance and dependence can develop in some patients, particularly during chronic administration.

Oedema is the pathological accumulation of fluid in tissue spaces. It can occur associated with various clinical conditions such as inflammation and inflammatory diseases. Current ways of controlling certain types of oedema include treatment with diuretic agents, but as with pain there is no single agent suitable for counteracting all types of oedema. There is therefore a constant need for alternative forms of treatment for oedema.

It has now surprisingly been found that 3,5-diamino-6-(2,3-dichlorophenyl)-1,2,4-triazine and its salts are effective in controlling pain and oedema. Accordingly, the present invention provides the use, in the preparation of a medicament for the prevention or treatment of pain or oedema, of 3,5-diamino-6-(2,3-dichlorophenyl)-1,2,4-triazine or a pharmaceutically or veterinarily acceptable acid addition salt thereof.

3,5-diamino-6-(2,3-dichlorophenyl)-1,2,4-triazine will hereinafter be referred to as compound A. Compound A and its salts will be referred to collectively as the present compounds. The present compounds are non-toxic at prophylactically and therapeutically effective doses. They have the important added advantage that tolerance to their analgesic effect does not develop, as demonstrated in Example 7 which follows.

Suitable acid addition salts of compound A include those formed with both organic and inorganic acids. Such acid addition salts will normally be pharmaceutically and veterinarily acceptable. Examples of such salts include those formed from hydrochloric, sulphuric, citric, tartaric, phosphoric, lactic, pyruvic, acetic, succinic, fumaric, maleic, methanesulphonic, ethanesulphonic, oxaloacetic and isethionic acids. The salts of isethionic acid are preferred since they possess particularly good solubility.

The present compounds may be prepared by a process which comprises cyclising a compound of formula (II):

and, if desired, converting compound A thus obtained into a pharmaceutically or veterinarily acceptable acid addition salt.

The cyclisation is typically carried out by heating the compound of formula II under reflux in an alkanol, preferably a $C_{1-4}$ alkanol, for example methanol or ethanol, in the presence of a strong base, for example potassium hydroxide. The process may, for instance, be carried out as described in Example 1 of EP-A-0021121. The optional subsequent step of converting the compound A into an acid addition salt is performed by a conventional method, for example by treatment with the appropriate acid at ambient temperature. The salt with isethionic acid may be prepared, for instance, as described in EP-A-0247892, in particular in Example 3.

The starting compound of formula II may be prepared by the method described in U.S. Pat. No. 3,637,688.

In mechanistic studies compound A has been shown at anti-convulsant brain concentrations to inhibit the release of excitatory amino acids, principally glutamate (Leach, M. J. et al (1986), Epilepsia 27, 490–497; Zhu, S. G. and McGee, E. G. (1990), Neuroci. Lett. 112: 348–351). Glutamate functions as an important neurotransmitter in the mammalian central nervous system, and it has also been identified as having specific actions in the peripheral nervous system. The known anti-convulsant effect of compound A has therefore been ascribed to its ability to act as an inhibitor of glutamate release.

Attempts have been made to classify different types of pain. Amongst those classes which have been broadly identified, but which nevertheless overlap to an extent, are acute pain and chronic pain.

A definition of acute pain (Halpern, 1984, Advances in Pain Research and Therapy, Vol. 7, Ed. C. Bendetti et al, page 147), which is not however limiting, is as a constellation of unpleasant sensory, perceptual and emotional experiences of certain associate autonomic (reflex) responses, and of psychological and behavioural reactions provoked by injury or acute disease. Tissue injury provokes a series of noxious stimuli which are transduced by nociceptors to impulses transmitted to the spinal cord and then to the upper part of the nervous system. Examples of acute pain are dental pain, post-operative pain, obstetric pain, headaches, neuralgia and myalgia.

A definition of chronic pain (Halpern, 1984, ibid.), also not limiting, is pain that persists beyond the usual course of an acute disease or beyond a reasonable time for an injury to heal. Chronic pain is typically a result of persistent dysfunction of the nociceptive pain system. Examples of chronic pain include trigeminal neuralgia, post-herpetic neuralgia (a form of chronic pain accompanied by skin changes in a dermatomal distribution following damage by acute Herpes Zoster disease), diabetic neuropathy, causalgia, "phantom limb" pain and pain associated with osteoarthritis, rheumatoid arthritis and cancer. Some of these, for example trigeminal neuralgia, diabetic neuropathic pain, causalgia, phantom limb pain and central post-stroke pain, have also been classified as neurogenic pain. One non-limiting definition of neurogenic pain is pain caused by dysfunction of the peripheral or central nervous system in the absence of nociceptor stimulation by trauma or disease.

Physiological and pathological pain have been defined in terms of their origin in the plasticity of the nervous system. The latter is defined in turn as the alteration in structure or function of the nervous system caused by development, experience or injury and can be either adaptive or maladaptive (Cervero, F. (1991) Eur. J. Neurosci. Suppl. 4: 162). Adaptive plasticity underlies the ability of the nervous system to compensate for damage or to produce changes in function which are appropriate to environmental change. Physiological pain, considered to be a sensation which reflects specific peripheral stimuli, is based on adaptive plasticity.

Maladaptive plasticity comprises those changes in the nervous system which lead to a disruption of function and therefore effectively constitute a disease state. Pathological pain is considered to be a sensation resulting from changes within the nervous system which bring about an alteration in the way in which information from the periphery, some of which may be quite normal, is handled. Pathological pain is therefore based on maladaptive plasticity (Woolf, C. J. (1989) Br. J. Anaesth. 63: 139–146).

Maladaptive plasticity of the nociceptive system has also been shown, in experimental models, to be present in states of chronic pain. For instance, multiple injections of hyperalgesic substances such as $PGE_2$ into the rat paw have been shown to induce sustained hyperalgesia to mild pressure (e.g. Nakamura-Craig and Smith (1989), Pain 38: 91–98; Ferreira et al (1990), Pain 42: 365–371; Nakamura-Craig and Gill (1991) Neurosci. Lett. 124: 49–51).

The present compounds are active in animal models of pain and oedema, as shown in Examples 1 to 6 which follow. The invention therefore provides a method of treating or preventing pain or oedema in a mammal, the method comprising administering thereto a therapeutically effective amount of one of the present compounds. The present compounds can thus be used in the prophylactic or therapeutic treatment of pathological conditions in which pain or oedema occur. In this way pain and oedema can be controlled. The condition of a human or animal can thereby be improved.

The present compounds have utility in preventing and treating different types of pain including chronic pain and acute pain. Examples of chronic pain which the present compounds can be used to prevent or treat include trigeminal neuralgia, post-herpetic neuralgia, painful diabetic neuropathy, causalgia, central post-stroke pain, "phantom limb" pain, atypical facial pain, back pain, headaches, neuralgia and pain associated with osteoarthritis, rheumatoid arthritis and cancer. Trigeminal neuralgia and post-herpetic neuralgia are particularly preferred.

Examples of acute pain which the present compounds can be used to prevent or treat include dental pain, post-operative pain, obstetric pain, headaches, neuralgia and myalgia. In particular, the present compounds can be administered pre-operatively to counteract the acute pain associated with surgical operations, including dental surgery, and labour pain. In one preferred embodiment the method of the invention comprises administering a therapeutically effective amount of one of the present compounds to a patient prior to a dental operation, for example a tooth extraction. Virtually no analgesic agents currently in use are effective in controlling pain when administered pre-operatively. It is therefore particularly surprising that the present compounds are effective when used in this way.

The present compounds also have utility in preventing and treating oedema, in particular oedema associated with inflammation. The present compounds are therefore particularly useful in preventing or treating oedema associated with inflammatory bowel disease, inflammatory arthritides disease, inflammatory vascular disease, post-operative inflammation and post-injury inflammation.

The present compounds are non-toxic at prophylactically and therapeutically effective doses. The orientative acute toxicity ($LD_{50}$) for compound A in mice is 250 mg/kg p.o. and in rats is 640 mg/kg. These are the dose levels at which 50% of the animals survive 10 days after administration of compound A.

The present compounds can be administered in a variety of dosage forms including those for oral, rectal, parenteral (such as subcutaneous, intramuscular and intravenous) epidural, intrathecal, intra-articular, topical and buccal administration.

The present compounds may be administered in any of the above dosage forms at a dose of from 1 mg/kg to 30 mg/kg per day, for example 5 mg/kg to 10 mg/kg, suitably 8 mg/kg to 10 mg/kg. For parenteral administration the range of 5 mg/kg to 10 mg/kg, for example 8 mg/kg to 10 mg/kg is particularly suitable. The dose range for adult humans will depend on a number of factors including the age, weight and condition of the patient and the administration route. A typical dosage regimen is from 20 mg to 2400 mg per day, typically from 350 mg to 1050 mg per day, preferably from 600 mg to 800 mg per day. It may in some situations be advantageous, since the present compounds are long-acting, to administer an initial dose of 70 mg to 2400 mg on the first day of treatment and then a lower dose of 20 mg to 1200 mg on subsequent days.

The present invention further provides a composition comprising a pharmaceutically or veterinarily acceptable carrier or diluent and, as an active principle, one of the present compounds. The composition can be prepared using conventional methods and administered in a pharmaceutically acceptable form.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavouring, preserving, suspending, thickening, or emulsifying agents can be included. When a suspension is prepared in water according to the present invention at least one of such agents will be present.

Other compounds which may be included by admixture are, for example, medically inert ingredients, e.g. solid and liquid diluents, such as lactose, dextrose, saccharose, cellulose, starch, or calcium phosphate, for tablet or capsules; olive oil or ethyl oleate for soft capsules; water or vegetable oil for suspensions or emulsions; lubricating agents such as silica, talc, stearic acid, magnesium or calcium stearate and/or polyethylene glycols; gelling agents, such as colloidal clays; thickening agents, such as gum tragacanth or sodium alginate; binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dye-stuffs; sweeteners; wetting agents such as lecithin, polysorbates or laurysulphates; and other therapeutically acceptable accessory ingredients, such as humectants, preservatives, buffers and antioxidants, which are known additives for such formulations.

Liquid dispersions for oral administration may be syrups, emulsions and suspensions. The syrups may contain as carrier, for example, saccharose or saccharose with glycerol and/or mannitol and/or sorbitol. In particular a syrup for diabetic patients can contain as carriers only products, for example sorbitol, which do not metabolise to glucose or which only metabolise a very small amount to glucose. The suspensions and the emulsions may contain a carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, the present compound may be encapsulated within liposomes.

The free base or a salt thereof may also be administered in its pure form unassociated with other additives, in which case a capsule, sachet or tablet, is the preferred dosage form.

Tablets and other forms of presentation provided in discrete units conveniently contain an amount of one of the present compounds which is effective at such dosage or a multiple thereof. For example, units may contain from 5 mg to 500 mg, but more usually from 10 mg to 250 mg of one of the present compounds.

The invention is further illustrated in the Examples which follow. In the accompanying drawings:

○ normal rats;

○ diabetic control;

■ diabetic rats treated with the 10 mg/kg of the present compound;

□ diabetic rats treated with 20 mg/kg of the present compound;

Δ diabetic rats treated with 40 mg/kg of the present compound.

■ control;

○ 10 mg/kg of the present compound;

Δ 30 mg/kg of the present compound;

∇ 100 mg/kg of the present compound.

FIG. 5 shows Δ reaction time in seconds (y axis) against time in days (x axis) for compound A at dose levels of 20, 50 and 100 mg/kg, a control (-○-○-) and saline (-□-□-) in the Randall-Sellito rat paw pressure test of Example 5a.

EXAMPLE 1

Testing of compound A in a neuropathic pain model in diabetic rats

The analgesic effect of compound A was demonstrated in an experimental model of neuropathic pain in diabetic rats using the procedure described by Wuarin-Bierman et al, Diabetologia 30, 653–658 (1987).

Male Wistar-strain rats (200–250 g) were treated with streptozotocin (70 mgkg$^{-1}$ i.p.). Three to four weeks after treatment, blood glucose concentrations were measured by tail clip sampling. Streptozotocin-treated rats with blood glucose levels of >12.0 mmol l$^{-1}$ were considered diabetic. Paw withdrawal response (reaction times,s) to paw pressure was measured using a modification of the Randall-Selitto test (Randall, L. O. and Selitto, J. J. (1957). Arch. Int. Pharmacodyn, 111, 409–419) in both diabetic rats and saline-treated (non-diabetic) controls before, and at various times for up to 24 hours after drug treatment. The modification involved using a constant paw pressure of 40 mmHg instead of the increasing paw pressure employed in the standard Randall-Selitto test. Reaction time to paw pressure in diabetic rats prior to treatment was significantly lower than that of non-diabetic controls (means=s.e. mean 13.6±0.2s, n=102 compared to 26.4±0.3s, n=45; p<0.001). Indomethacin (1–10 mgkg$^{-1}$ p.o.) had no effect on reaction time whereas morphine, (0.2, 0.5 or 1.0 mgkg$^{-1}$ s.c.) significantly (p<0.001) increased reaction times in diabetic rats at 1 hour after dosing to 17.6±0.7, 22.8±1.2 or 28.2±1.0s (n=8), respectively. Significant analgesia was still present 5 hours after morphine, (1.0 mgkg$^{-1}$, reaction time, 18.7±1.0s, n=8; p<0.05). This dose of morphine also increased reaction times in non-diabetic rats 1 hour after dosing (28.8±1.3s, n=4; p<0.05). Compound A (20 or 40 mgkg$^{-1}$ p.o.) induced significant analgesia at 1 hour after dosing (reaction times, 18.7±1.4 and 23.9±0.9s, n=8, respectively; p<0.01) which lasted for at least 5 hours (reaction times; 17.3±1.1 and 23.0±0.8s, n=7, respectively; p<0.01) in diabetic rats but had no effect in non-diabetic controls. Paw pressure reaction times had returned to the values pre-administration of compound A by 24 hours after dosing. Blood glucose concentrations were unaffected by any analgesic treatment.

Figure 1:
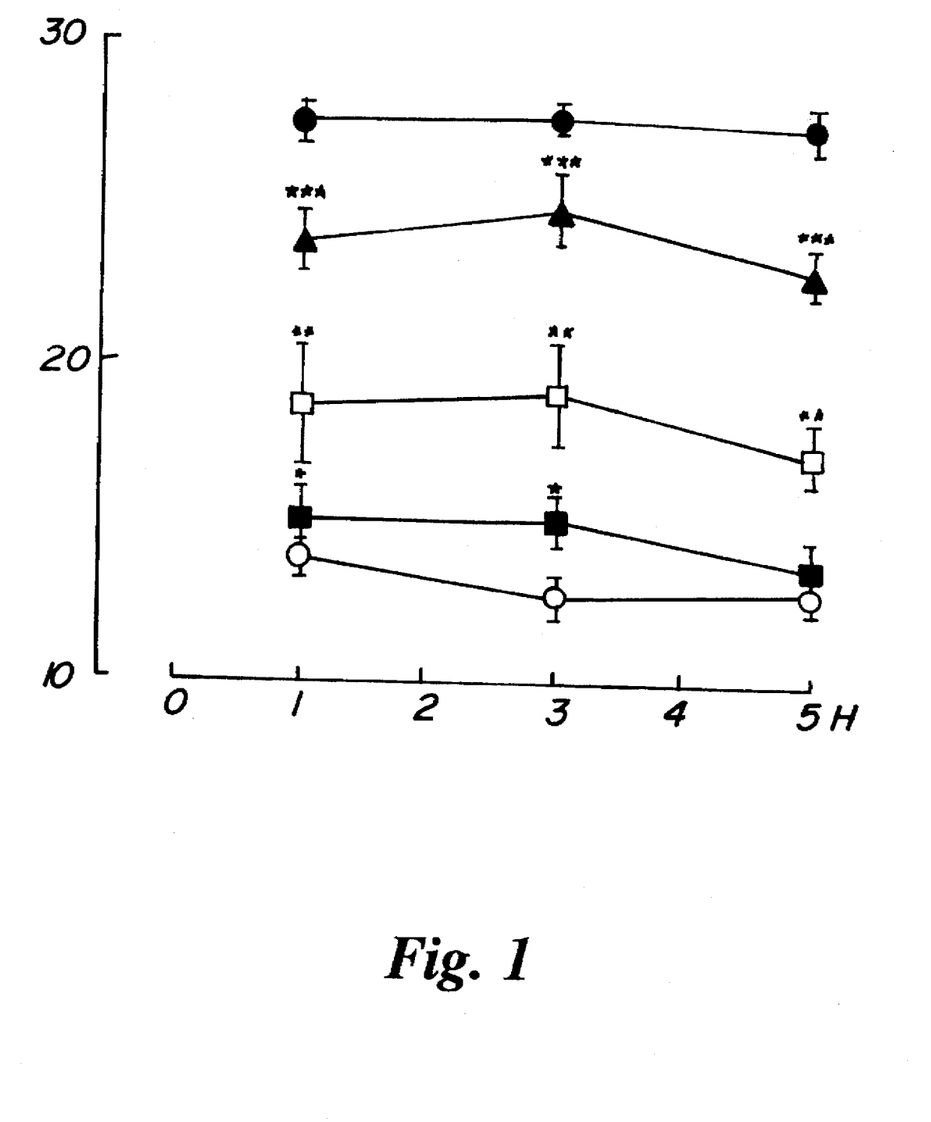
FIG. 1 shows reaction time (y axis) against time (x axis) in a test of the effect of compound A in a neuropathic pain model in diabetic rats (Example 1). The curves are as follows.

The results obtained for compound A and illustrated in FIG. 1 show the compound to have activity as an analgesic in the treatment of neuropathic pain.

EXAMPLE 2

Testing of compound A against oedema

Compound A was tested against carragheen-induced paw oedema in rats, as follows:

Animals

Male Wistar-strain rats were supplied by Charles River UK Ltd. one week prior to use. They were housed in groups of 5 under controlled environmental conditions. ambient temperature 20±1° C., relative humidity 55% and photoperiod 07.00–19.00 h. Pelleted diet and drinking water were available at all times except that food was removed 18 hours prior to dosing. At the time of use the rats weighed 150–190 g.

Materials

A 1% suspension of carragheen was prepared by ball-milling a weighed quantity with zirconium rollers in 0.85% saline, overnight at 4° C. using a Pascall ball-mill. Test compounds were prepared as suspensions in 0.25% methylcellulose (celacol) in a similar manner. Further dilution was carried out in celacol as required to give a range of doses.

Procedure

Compound A, or celacol as control, was administered orally in a dose volume of 5.0 ml/kg to groups of 5 rats. One hour later, 100 µl carragheen 1% was injected sub-plantar into the right hind paw of each rat. Ventral-dorsal paw thickness was measured using dial callipers (Mitutoyo) before drug treatment and again at intervals of paw injection. The carragheen-induced increase in paw thickness was calculated at each time interval and treatment group mean±sem compared to that of controls measured concurrently using Student t-test. Probability values ≦0.05 were considered significant.

Figure 2:
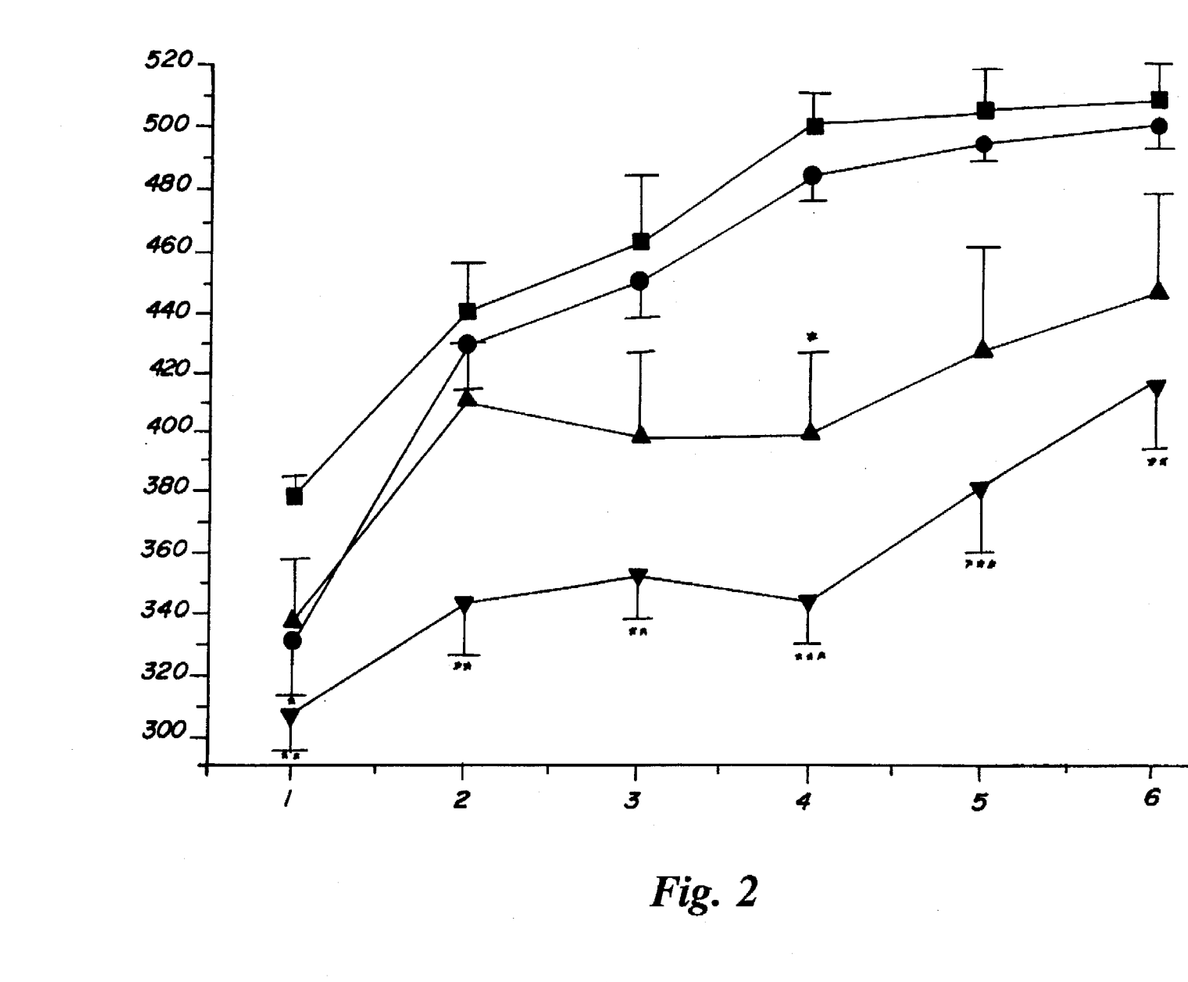
FIG. 2 shows the increase in paw thickness (mm×100, y axis) against time in hours (x axis) in a test of the effect of compound A on carragheen-induced oedema in the rat paw (Example 2). Curves are as follows.

The results obtained for compound A are illustrated in FIG. 2.

EXAMPLE 3

Testing of compound A against carragheen-induced hyperalgesia

Compound A was tested against carragheen-induced hyperalgesia in a rat model, as follows:

Animals and materials were as described for Example 2, except that a 0.1% suspension of carragheen was used.

Procedure

Each rat received a sub-plantar injection of 100 µl carragheen 0.2% in the right hind paw. The test compound, or celacol as control, was administered orally in a dose volume of 5.0 ml/kg to groups of 5 rats at either 1 hour prior to, or 1 hour after, paw injection. Before drug treatment and again at 3 hours after carragheen, a constant pressure of 40 mm Hg was applied to each hind paw and the flinch/ withdrawal time recorded. Treatment group means Δ reaction times were calculated and compared to that of controls using Student t-test. Probability values ≦0.05 were considered significant.

Figure 3A:
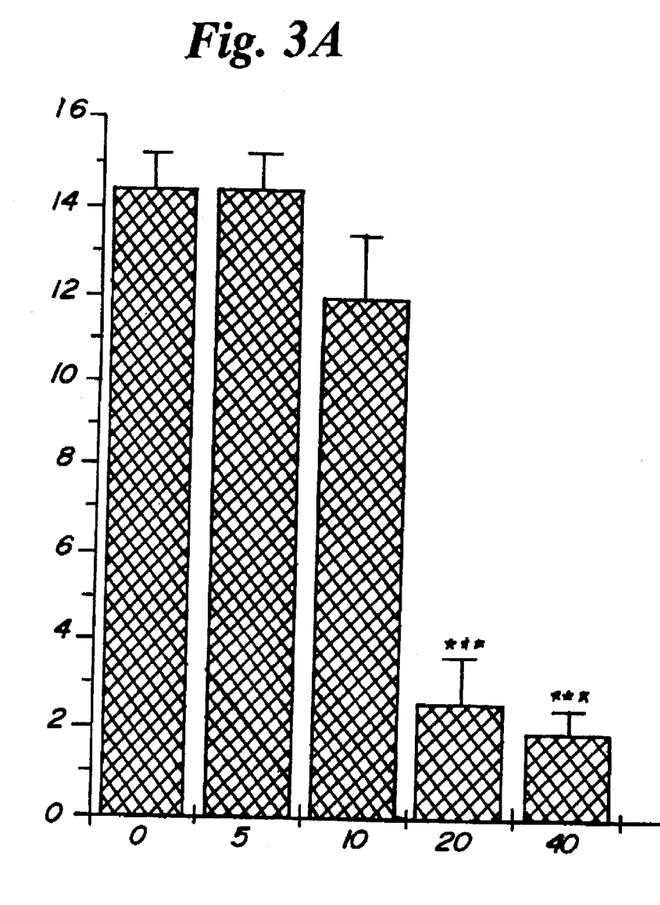
FIG. 3 shows Δ reaction time in seconds (y axis) against dose of compound A in mg/kg (x axis) in a carragheen-induced hyperalgesia test in the rat (Example 3). Plot A is 1 hour before administration of the compound, and plot B is 1 hour after.
Figure 3B:
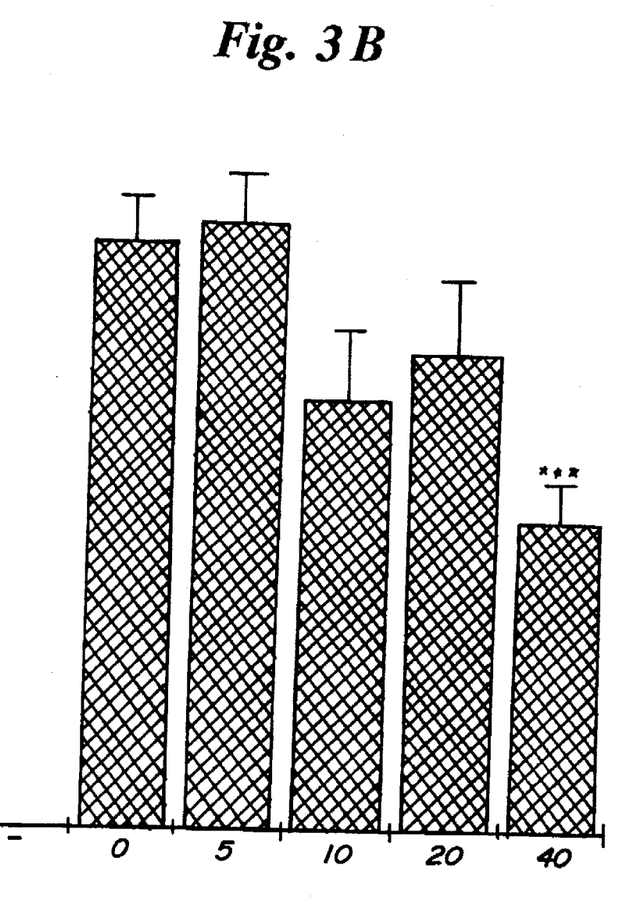

The results are illustrated in FIG. 3.

EXAMPLE 4

Testing of compound A in an acute pain model in the rat

The effect of compound A on the motor unit activity of Longus Digitorum flexor muscle to noxious stimulus in the anaesthetized rat was tested as follows:

Male Wistar rats (250–350 g) were anaesthetized with pentobarbitone (Sagatal, RMB Animal Health, Dagenham, Essex U.K., 60 mgkg$^{-1}$, i.p.). Femoral and carotid cannulations were performed for i.v. administration and arterial blood pressure monitoring, respectively. The contralateral hind leg with respect to the femoral cannula was fixed in a plastic holder with Plaster of Paris. Noxious pinches were applied to the fourth toe of the hind paw by a pneumatic pincher (duration 15 second every 3 minutes). Electrical activity was recorded differentially using two teflon coated platinum/iridium microwires embedded in araldite in a stainless steel needle which was inserted into the muscle through a small incision in the skin.

Figure 4:
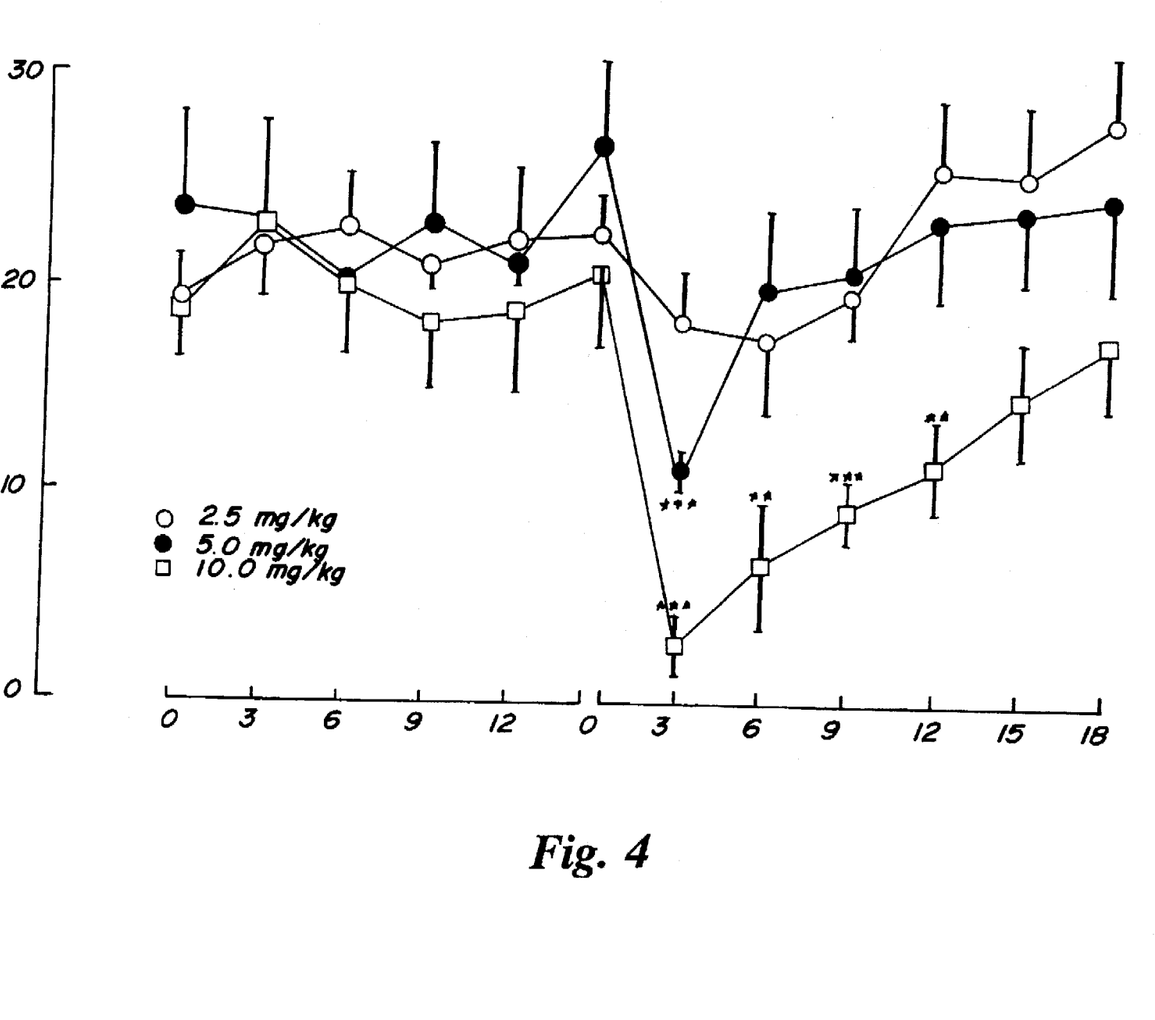
FIG. 4 shows the effect of compound A on evoked motor unit activity in the anaesthetised rat (Example 4), with spike rate in impulses/sec (y axis) against time in minutes (x axis).

Compound A was injected into the rats at time zero, 12 minutes after saline (i.v.). Measurements of motor unit activity (pinch response) were made each 3 minutes over an 18 min. period following administration of compound A. The results are shown in FIG. 4, presented as mean±s.e.m. of 5 animals. They demonstrate that, at 5.0 mg/kg i.v., compound A caused a short-lived reduction (48±9%, $p<0.001$, n=5) of motor unit activity 3 minutes after injection.

At a dose of 10 mg/kg, compound A inhibited pinch response by 86±16% (peak effect 3 minutes after administration). The effect remained significant up to 12 minutes after administration.

EXAMPLE 5

Testing of compound A against $PGE_2$ evoked hyperalgesia

The inhibitory effect of compound A on the development of $PGE_2$-evoked hyperalgesia was evaluated by a modification of the Randall-Selitto paw pressure model (Randall, L. O. and Selitto, J. J., ibid.) described in Ferreira S. H. et al, (1978) Eur. J. Pharmacol. 53, 39–48, in a series of tests on groups of 6 male Wistar rats (200–250 mg).

Multiple sub-plantar (S.pl) injections of 100 ng of Prostaglandin $E_2$ (Sigma Chemical Company, Poole, Dorset U.K.) were administered to the rats twice a day for 4 days. This induced a sustained hyperalgesia lasting for at least 5 days.

Figure 5:
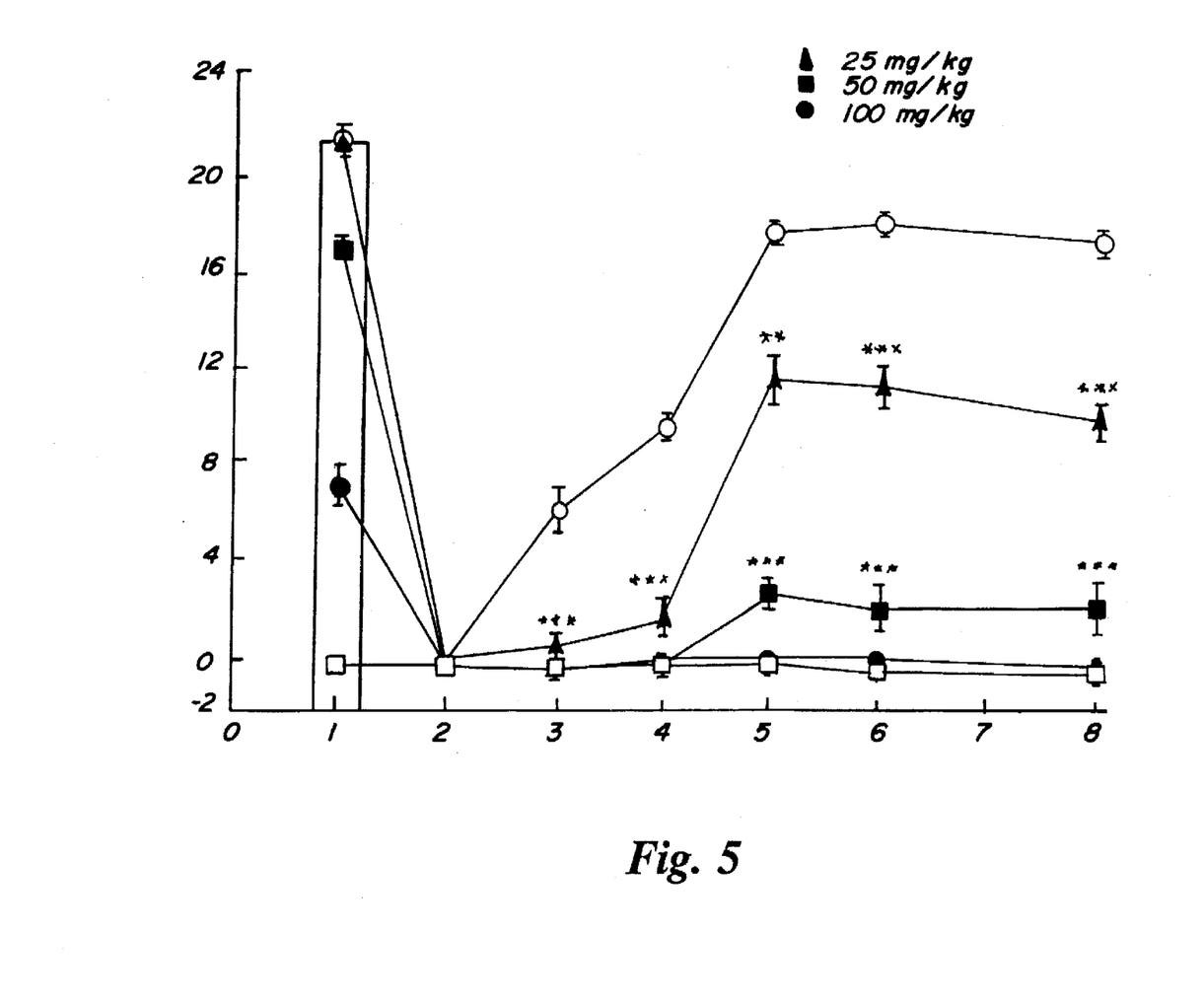

(a) A single oral dose of compound A was administered before the first injection of $PGE_2$. The intensity of hyperalgesia, measured as Δ reaction time (seconds), was recorded daily for 4 days after sustained hyperalgesia had been established. FIG. 5 shows the results presented as mean values±s.e.mean of 6 animals. Significant statistical difference from control $p<0.01$, *$p<0.001$. Five days after the commencement of multiple dosing with $PGE_2$ the % inhibition of hyperalgesia by compound A (20, 50 and 100 mg/kg) was 31±6%, 85±3% and 99±2%, respectively.

Figure 6:
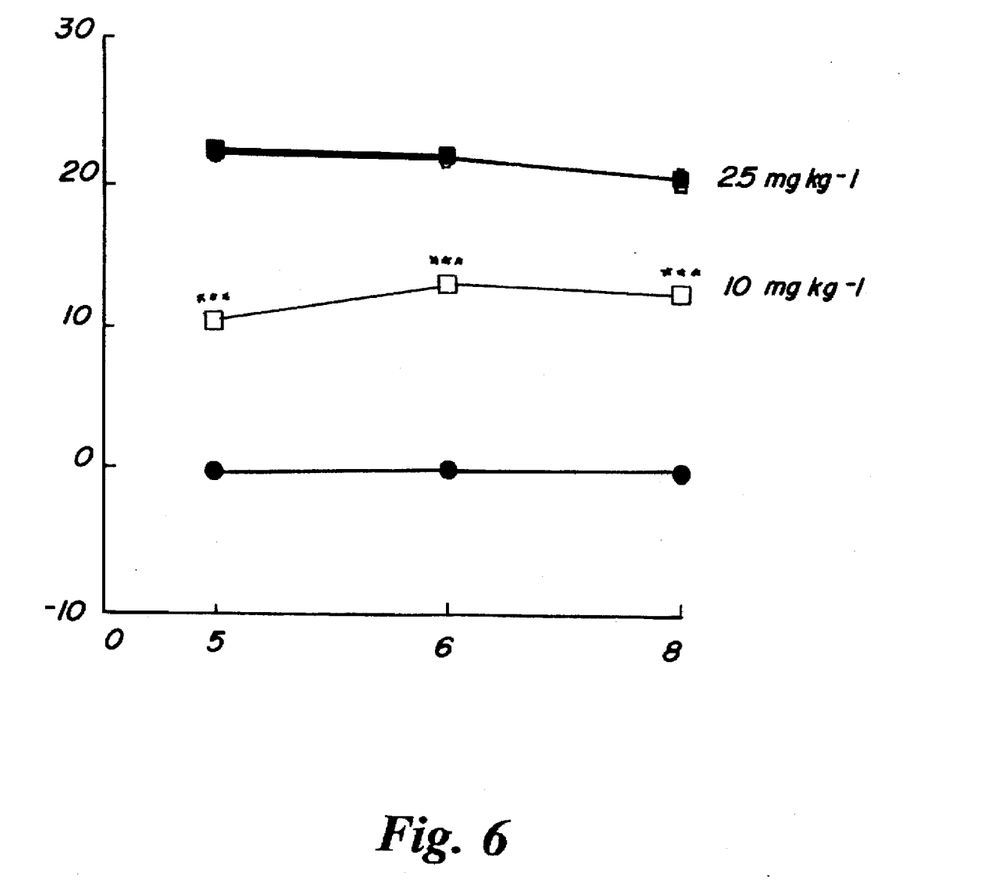
FIG. 6 shows Δ reaction time in seconds (y axis) against time in days (x axis) for compound A at dose levels of 2.5 mg/kg (-□-□-) and 10 mg/kg (-□-□-) compared with a control (-○-○-) and saline (-○-○-) in the test of Example 5b.

(b) Compound A was administered orally 1 hour before each sub-plantar injection of $PGE_2$. The intensity of hyperalgesia was recorded as described under (a) above. FIG. 6 shows the results as mean values±s.e. means of 6 animals. Significant statistical differences from control *$p<0.05$, ***$p<0.001$. Sustained hyperalgesia to $PGE_2$ is shown to be potently reduced by compound A at 10 mg/kg (40±3% inhibition, $p<0.001$, n=5).

Figure 7:
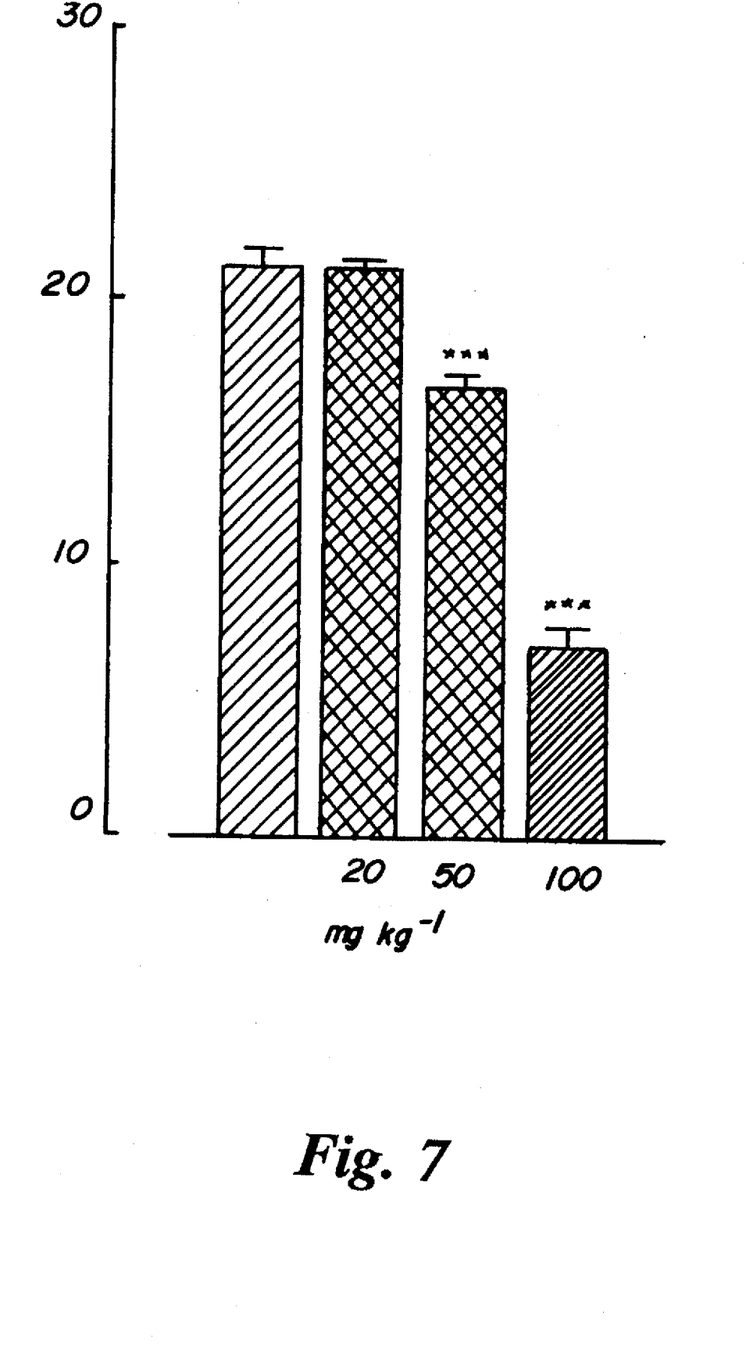
FIG. 7 shows Δ reaction time in seconds (y axis) against dose of compound A (x axis) in the test of Example 5c.

(c) Compound A was administered orally 1 hour before a single $PGE_2$ injection. Hyperalgesia was measured 3 hours after $PGE_2$ injection (as Δ reaction time) for compound A at dose levels of 20, 50 and 100 mg/kg and for a control. FIG. 7 shows the results as mean values±s.e. means of 6 animals. Significant statistical difference from control ***$p<0.001$.

Figure 8:
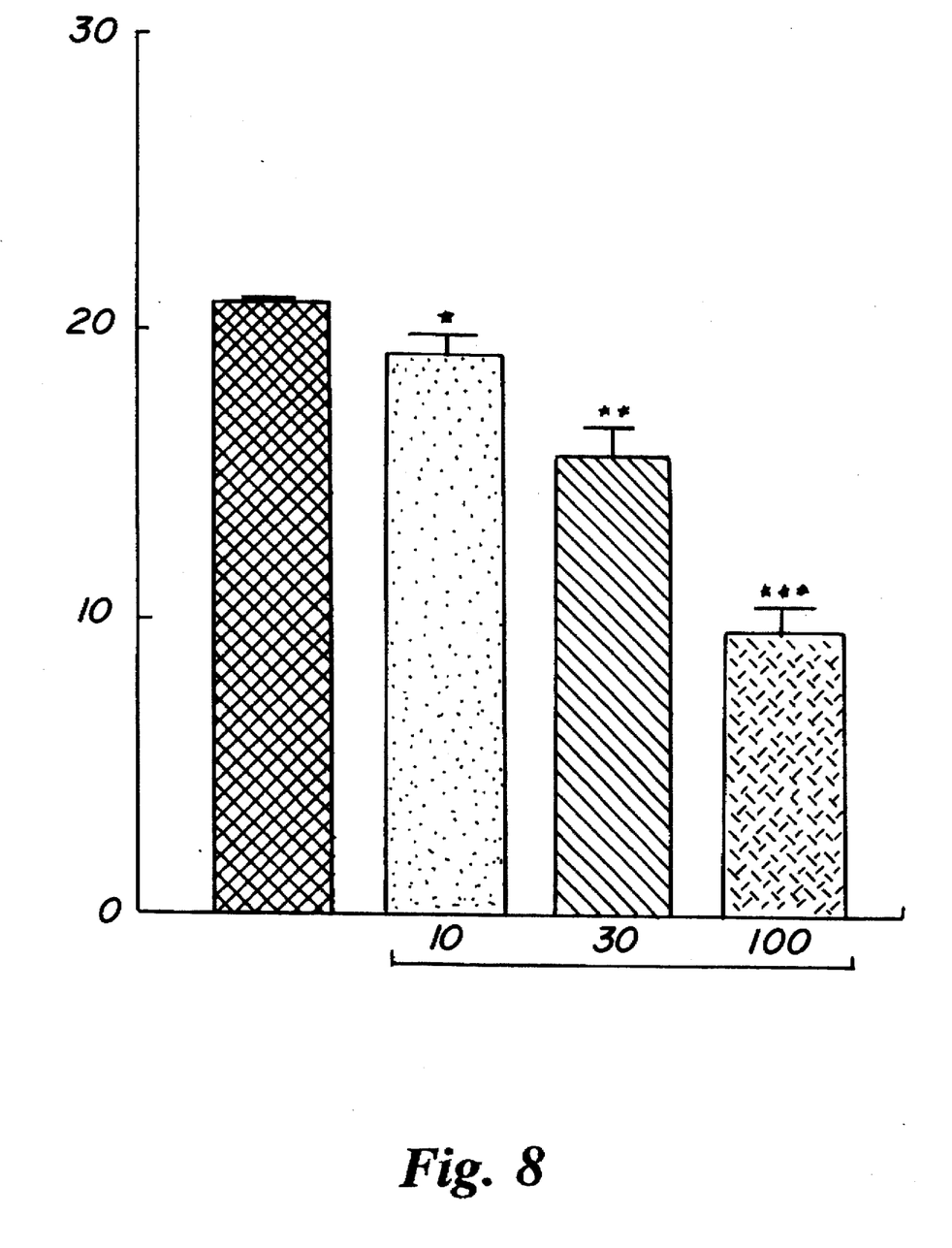
FIG. 8 shows Δ reaction time in seconds (y axis), for a control and for compound A at dose levels of 10, 30 and 100 mg/kg in the test described in Example 5d.

(d) Compound A was administered orally 2 hours after a single sub-plantar PGE$_2$ injection. Measurements of hyperalgesia as A Δ reaction times were made 3 hours after PGE$_2$ administration. FIG. 8 shows the results as mean values±s.e. mean of 6 animals. Significant difference from control *p<0.05; p<0.01; *P<0.001.

EXAMPLE 6

Testing of compound A against adjuvant-induced hyperalgesia

Compound A was tested against adjuvant-induced hyperalgesia as follows:
Animals

Male Wistar-strain rats were supplied by Charles River UK Ltd one week prior to use. They were housed in groups of 5 under controlled environmental conditions of ambient temperature 20±1° C., relative humidity 55% and photoperiod 07.00–19.00 h. Pelletted diet and drinking water were available at all times.
Materials Adjuvant was prepared by ball-milling a weighed quantity of mycobacterium butyricum in Freund's adjuvant incomplete (Sigma) with zirconium rollers overnight at 4° C. to give a 5.0 mg/ml suspension. The test compound was prepared as suspensions in celacol by ball-milling and then diluted as required.
Procedure Adjuvant was injected subcutaneously at the base of the tail of each rat in 2 sites of 50 μl. One group of rats received a similar volume of incomplete adjuvant as control. The test compound or celacol as control was administered orally in a dose volume of 5.0 ml/kg to groups of 5 rats once daily for up to 14 days, commencing either on day 1 (1 h prior to adjuvant) or an subsequent days, during the development of hyperalgesia. Reaction times (freezing reaction) to a constant pressure of 20 mmHg applied to each hind paw were recorded prior to injection of adjuvant and again at intervals on subsequent days for up to 14 days after. Treatment group mean±sem Δ reaction times for hyperalgesia were calculated and compared with those of controls measured concurrently using Student-test. Probability values≦0.05 were considered significant.

Figure 9:
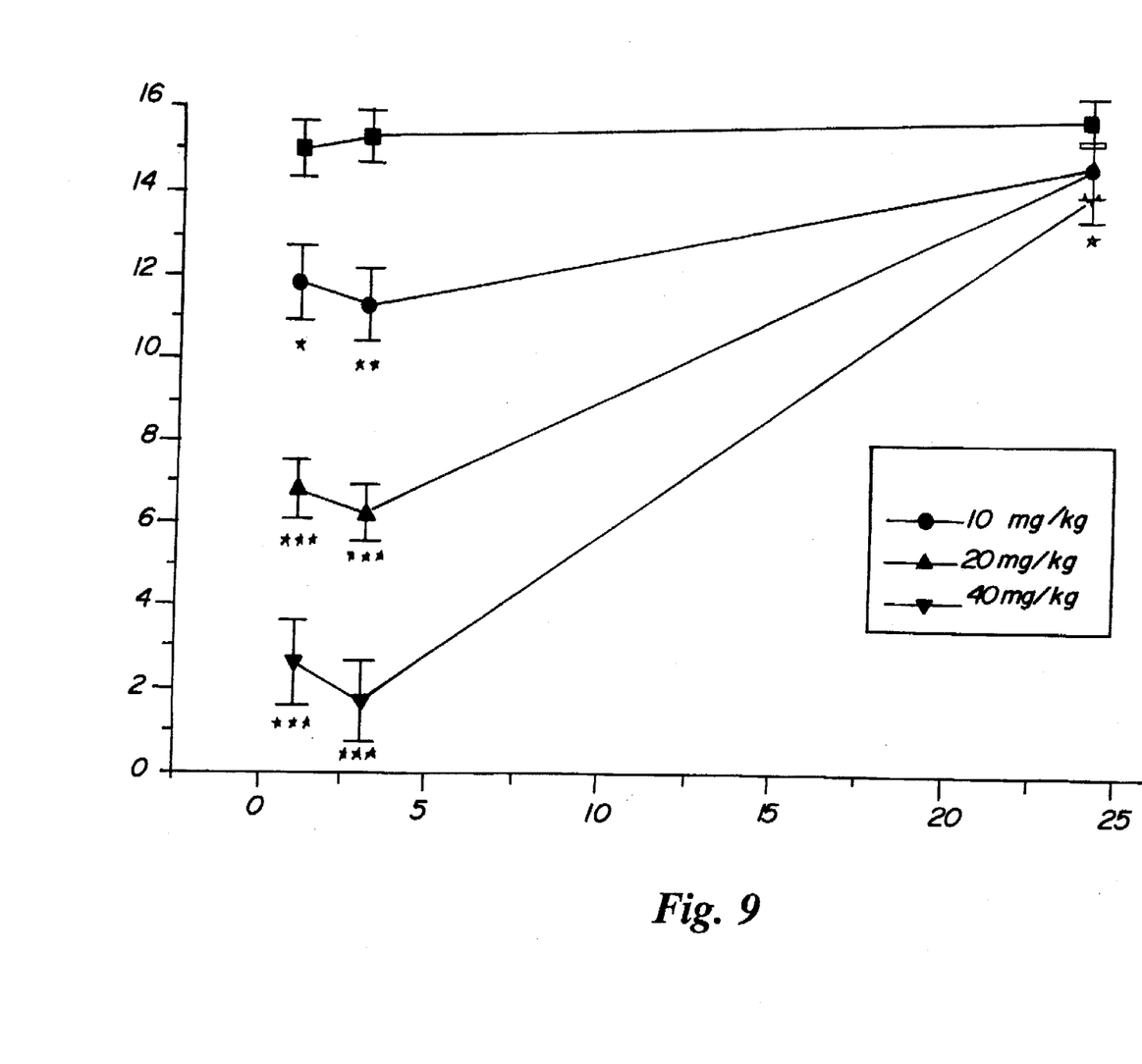
FIG. 9 shows Δ reaction time in hours on day 6 for a control (-■-■-) and for three dose levels of compound A in the test described in Example 6.

The results are shown in FIG. 9.

EXAMPLE 7

Tolerance does not develop to Compound A

Figure 10:
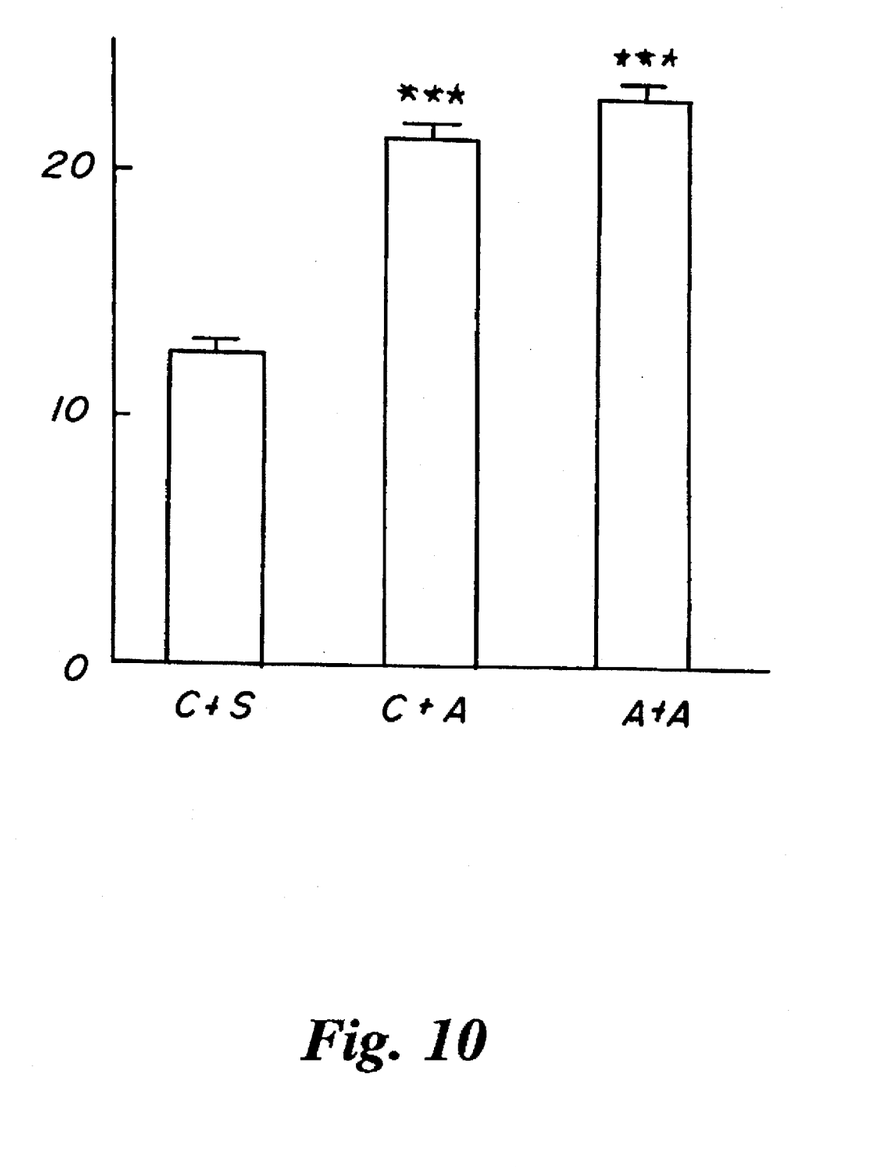
FIG. 10 shows reaction time in seconds (y axis) for rats treated as described in Example 7.

Diabetic male Wistar rats were treated with celacol (C) or compound A (20 mg/kg p.o.) twice daily for 4 days. On day 5 the animals were challenged with compound A (20 mg/kg p.o.) or saline (S) and their pain threshold determined as a function of reaction time. The results are shown in FIG. 10, presented as mean values±s.e. mean of the reaction time, S (n=6) for celacol+saline (C+S), celacol+compound A (C+A) and compound A+compound A (A+A). Significant difference from C+S is shown as ***p<0.001 (t test).

Since the observed analgesic effect of compound A is the same in rats treated for 5 days with compound A as in those treated only with celacol, tolerance to compound A clearly has not developed.

EXAMPLE 8

Pharmaceutical composition

Tablets for oral administration were formulated with the following ingredients;

| | |
|---|---|
| Compound A | 150 mg |
| Lactose | 200 mg |
| Maize starch | 50 mg |
| Polyvinylpyrrolidene | 4 mg |
| Magnesium stearate | 4 mg |

The active compound was mixed with the lactose and starch and granulated with a solution of the polyvinylpyrrolidone in water. The resulting granules were dried, mixed with magnesium stearate and compressed to give tablets of average weight 408 mg.

We claim:

1. A method of preventing or treating oedema in a mammal, in need thereof the method comprising administering thereto a therapeutically effective amount of a compound selected from 3,5-diamino-6-(2,3-dichlorophenyl)-1,2,4-triazine and the pharmaceutically and veterinarily acceptable acid addition salts thereof.

2. The method of claim 1 in which the salt administered is the isethionic acid addition salt.

3. The method of claim 1 in which the oedema is associated with inflammatory bowel disease, inflammatory arthritis disease, inflammatory vascular disease or with post operative inflammation or post injury inflammation.

4. A method of preventing or treating chronic pain in a mammal in need thereof, the method comprising administering thereto a therapeutically effective amount of a compound selected from 3,5-diamino-6-(2,3-dichlorophenyl)-1,2,4-triazine or a pharmaceutically acceptable acid addition salt thereof.

5. The method of claim 4 in which the salt administered is the isethionic acid addition salt.

6. A method of preventing or treating acute pain in a mammal in need thereof, the method comprising administering thereto a therapeutically effective amount of a compound selected from 3,5-diamino-6-(2,3-dichlorophenyl)-1,2,4-triazine or a pharmaceutically acceptable acid addition salt thereof.

7. The method of claim 6 in which the salt administered is the isethionic acid addition salt.

8. The method of claim 6 in which the pain is dental pain or post-operative pain.

* * * * *

UNITED STATES PATENT AND TRADEMARK OFFICE
CERTIFICATE OF CORRECTION

PATENT NO. : 5,712,277
DATED : January 27, 1998
INVENTOR(S) : Nakamura-Craig et al.

It is certified that error appears in the above-identified patent and that said Letters Patent is hereby corrected as shown below:

Title page,
Item [63], Related U.S. Application Data, should read
-- [63] Continuation of Ser. No. 284,497, filed as PCT/GB93/000341 February 18, 1993. --

Signed and Sealed this

Second Day of August, 2005

JON W. DUDAS
*Director of the United States Patent and Trademark Office*